United States Patent [19]

Nakamura

[11] Patent Number: 5,609,565
[45] Date of Patent: Mar. 11, 1997

[54] ARTICULATED TOOL-HOLDING ARM

[75] Inventor: Katsushige Nakamura, Tokyo, Japan

[73] Assignee: Mitaka Kohki Co., Ltd., Tokyo, Japan

[21] Appl. No.: 512,225

[22] Filed: Aug. 7, 1995

[30]  Foreign Application Priority Data

Sep. 8, 1994 [JP] Japan .................................. 6-187614

[51] Int. Cl.⁶ ................................................. A61B 17/02
[52] U.S. Cl. ........................ 600/229; 600/102; 600/227;
600/228; 285/166; 403/56; 403/71; 403/83;
248/278.1
[58] Field of Search ................................... 600/103, 227,
600/228, 229, 230, 231; 285/166; 248/278.1,
279.1; 403/52, 56, 57, 72, 76, 77, 83, 90;
269/909, 74, 75

[56]  References Cited

U.S. PATENT DOCUMENTS

| 2,608,192 | 8/1952 | Heitmeyer et al. . | |
| 3,638,973 | 2/1972 | Poletti | 600/229 X |
| 3,858,578 | 1/1975 | Milo . | |
| 4,143,652 | 3/1979 | Meier et al. . | |

FOREIGN PATENT DOCUMENTS 4307589  9/1993  Germany .

62-327  1/1987  Japan .

OTHER PUBLICATIONS

English language abstract of Japanese Specification for invention titled Locating Apparatus for Cranial Operating Site, Pre–Examination of Patent Publication No. Sho 62–327, Jan. 6, 1987.

*Primary Examiner*—Richard J. Apley
*Assistant Examiner*—Beverly M. Flanagan
*Attorney, Agent, or Firm*—Michael D. Bednarek; Kilpatric & Cody, L.L.P.

[57]  ABSTRACT

Each pivotal shaft normally urged in one direction by the urging means drives the movable barrel to push the pressure spring, so that the clutch disposed either to the inner ball or to the outer ball in each joint is brought into press contact with the other ball to lock the joint. Accordingly, once the holding arm holds a tool, the holding force of the arm does not decline with time. Since the pressure applied to the pressure spring by the movable barrel is released by turning the pivotal shaft in the opposite direction by the driving means, each joint assumes an unlocked state. Thus, the tool held at the free end portion of the holding arm can be moved to a desired position, and also the holding position can be changed very easily.

4 Claims, 6 Drawing Sheets

5,609,565

ARTICULATED TOOL-HOLDING ARM

BACKGROUND OF THE INVENTION

1. Field of the Invention

This invention relates to an articulated arm for holding a tool.

2. Description of the Prior Art

Recently, various kinds of tools are utilized in the medical field. For example, in the field of brain surgery a tool referred to as brain spatula is used. The brain spatula is used for pressing the brain partly during brain surgery to provide wider vision of the site to be operated. The brain spatula is held immovably by a special holding arm with the brain being pressed by the brain spatula, and if the force of the holding arm to hold the brain spatula is insufficient, the brain spatula is pushed back gradually by the brain during the operation. Accordingly, the location of the brain spatula must be adjusted occasionally. Even if the holding arm has sufficient holding force, the position or angle of the brain spatula must frequently be changed for convenience' sake during the surgery. Thus, the brain spatula holding arm should have such operability as to quickly respond to such frequent changes.

That is, the holding arm for holding a tool such as a brain spatula is required to have a function of holding a tool securely at a desired position with no reduction in the holding force with time and allowing easy change of the holding position. Incidentally, medical tools which are to be held by such holding arm include any conceivable tools and devices, in addition to brain spatulas, such as an aspiration tube, an ultrasonic echo probe and an endoscope. Further, there are innumerable tools and devices which also require such secured holding in other fields than medicine.

The present inventor accomplished the present invention noting such prior art technique and provides an articulated tool holding arm which functions as described above.

SUMMARY OF THE INVENTION

According to a first aspect of the invention, the articulated tool holding arm comprises a plurality of tubular arms connected to one another at joints each consisting of an outer ball and an inner ball slidably fitted therein;

a handle for holding a tool, attached to the foremost end of the thus connected tubular arms;.

pivotal axes penetrating the arms such that they may be connected to one another at the end portions in the joints, respectively, to be able to transmit turning motions to one another;

a clutch disposed to either the inner ball or the outer ball in each joint, the clutch being pressed by a pressure spring to be brought into contact with the other ball; and a movable barrel engaged with an external thread formed near the end portion of each pivotal shaft;

wherein each of the pivotal axes is designed to be normally urged to turn in one direction by an urging means to allow the movable barrel to press the pressure spring; whereas the pressure applied to the pressure spring by the movable barrel is adapted to be releasable by turning the pivotal shaft by a driving means in the opposite direction against the urging force of the urging means.

According to the first aspect of the invention, since each pivotal shaft normally urged in one direction by the urging means drives the movable barrel to push the pressure spring, the clutch disposed either to the inner ball or to the outer ball in each joint is brought into press contact with the other ball to lock the joint. Accordingly, once the holding arm holds a tool, the holding force of the arm does not decline with time. Since the pressure applied to the pressure spring by the movable barrel is released by turning the pivotal shaft in the opposite direction by the driving means, each joint assumes an unlocked state. Thus, the tool held at the free end portion of the holding arm can be moved to a desired position, and also the holding position can be changed very easily.

According to a second aspect of the invention, the urging means for turning each pivotal shaft in one direction is a plurality of coil springs, and the driving means for turning the pivotal shaft in the opposite direction is hydraulic pressure.

According to a third aspect of the invention, the handle is provided with a couple of levers which form a predetermined angle and also a pair of links having a connecting point which shifts when the levers are held closer to each other, with a wire being connected at one end to the connecting point and inserted through the pivotal axes; and the driving means for turning the pivotal axes in the opposite directions is controlled at the other end of the wire.

The gist of the present invention is not limited to the above description, and the objects, advantages, features and uses of this invention may best be understood by reference to the following description taken in conjunction with the accompanying drawings. It should be understood that the present invention may be modified suitably without departing from the spirit or scope of the invention and that such modifications are all included within the scope of the invention.

DETAILED DESCRIPTION OF PREFERRED EMBODIMENT

A preferred embodiment of the invention will be described below with reference to the attached drawings. It should be appreciated here that in the following description the directions forward (front), backward (rear), leftward (left side) and rightward (right side) are represented by the directions A, B, C and D, respectively.

Figure 1:
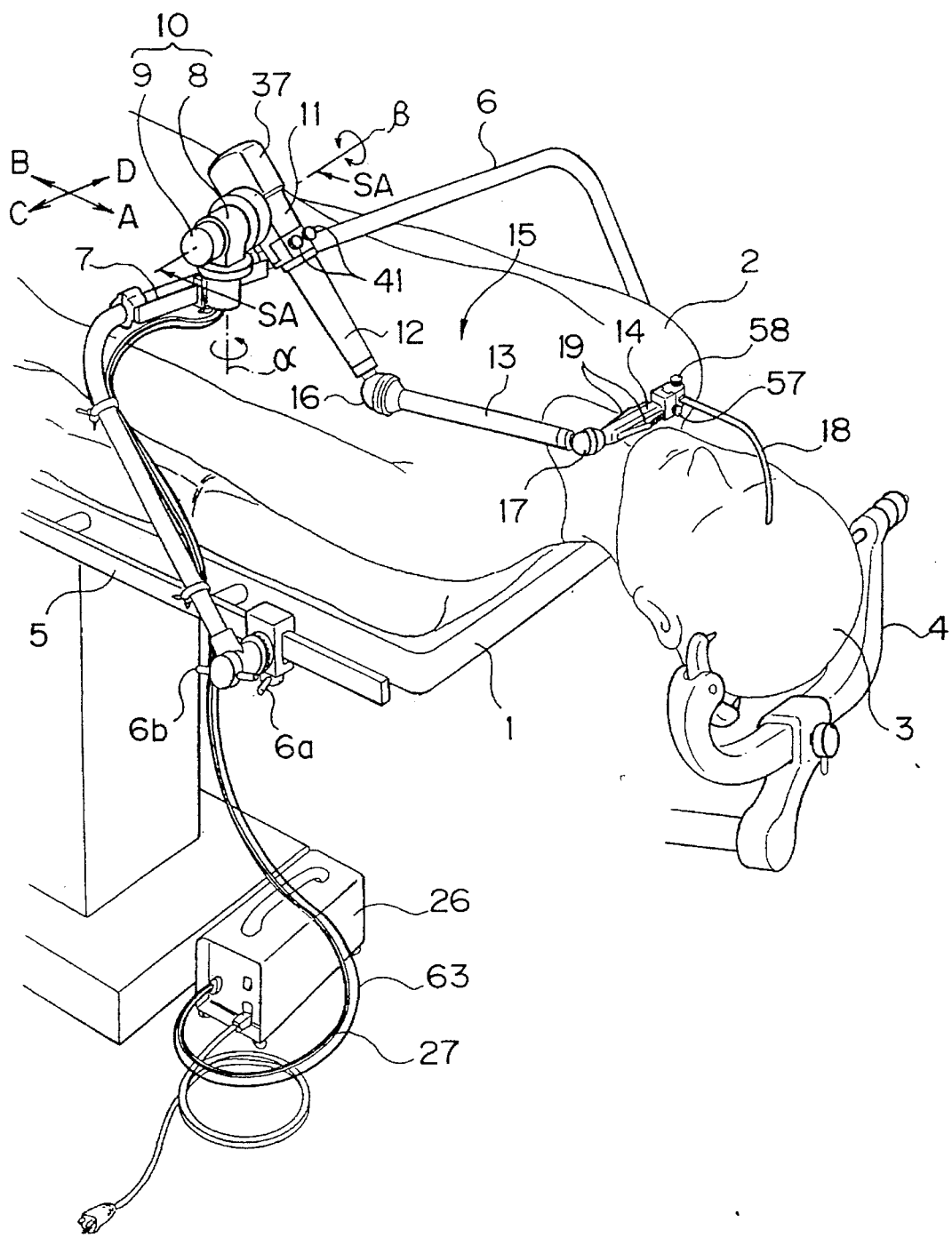
FIG. 1 is an overall view of the articulated tool holding arm according to one embodiment of the invention.

First, the overall structure of the articulated tool holding arm will be described referring to FIG. 1. The reference number 1 denotes a surgical bed on which a patient 2 lies. The head 3 of the patient 2 is immobilized by a holder 4. The surgical bed 1 has side guards 5 on each side with an overhang arm 6 being extended across these side guards 5 to be slidable therealong. The position of the overhang arm 6 can be changed forward or backward along the side guards 5 by turning adjust levers 6a. Meanwhile, the angle of the overhang arm 6 can also be changed by operating other adjust levers 6b.

The overhang arm 6 has a rail 7 formed partly thereon, on which a rotary section 10 consisting of a vertical part 8 and a horizontal part 9 is fitted. The vertical part 8 has a dovetail groove 8a which is engaged with the rail 7. The horizontal part 9 is designed to be rotatable horizontally on the axis α of the vertical part 8.

An arm supporting section 11 is connected to the horizontal part 9 to be rotatable vertically on the horizontal axis β. A holding arm 15 consisting of a first arm 12, a second arm 13 and a handle 14 is attached to the arm supporting section 11. The first arm 12 and the second arm 13 are connected to each other via a first joint 16; whereas the second arm 13 and the handle 14 are connected to each other via a second joint 17. The first arm 12 is removably fixed to the arm supporting section 11 such that the holding arm 15 can entirely be removed from the arm supporting section 11. Further, a brain spatula 18 is attached to the free end portion of the handle 14, and a pair of levers 19 are disposed on each side of the handle 14. These levers 19 serve as a switch for allowing the holding arm 15 to assume an unlocked state. That is, in this holding arm 15, the axis a of the vertical part 8, the axis β of the horizontal part 9 and the joints 16,17 are adapted to assume unlocked states only when the levers 19 are pressed by holding the handle 14 with a hand, so that the position and angle of the brain spatula 18 can be changed freely. Meanwhile, when the levers 19 are not pressed, the axes α and β and the joints 16,17 are adapted to assume locked states, so that the position and the angle of the brain spatula 18 can be fixed.

The structure of the articulated tool holding arm for obtaining such performance will now be described part by part.

Figure 4:
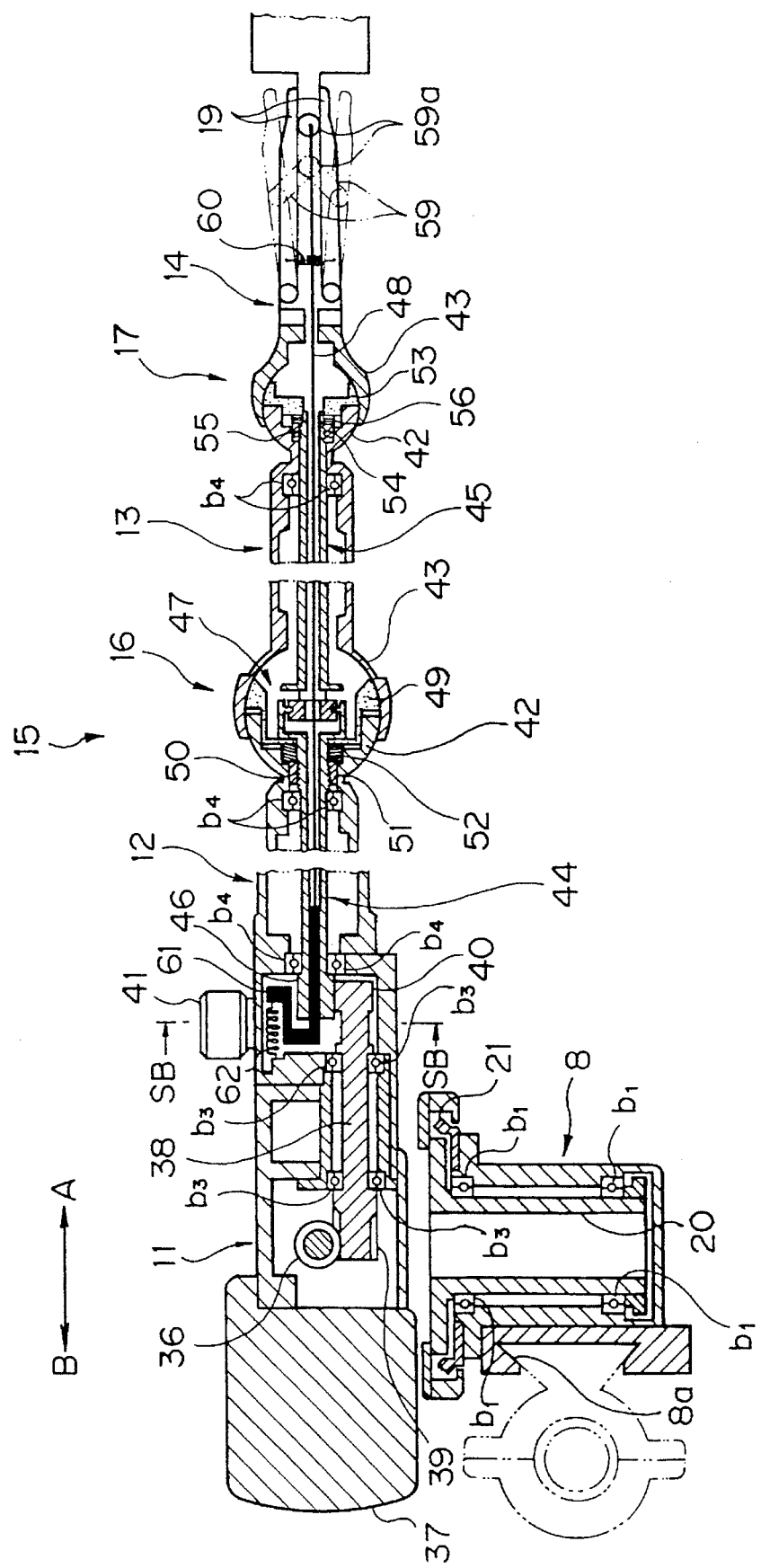
FIG. 4 is a cross-sectional view showing a vertical part, an arm supporting section, arms and a handle.
Figure 5:
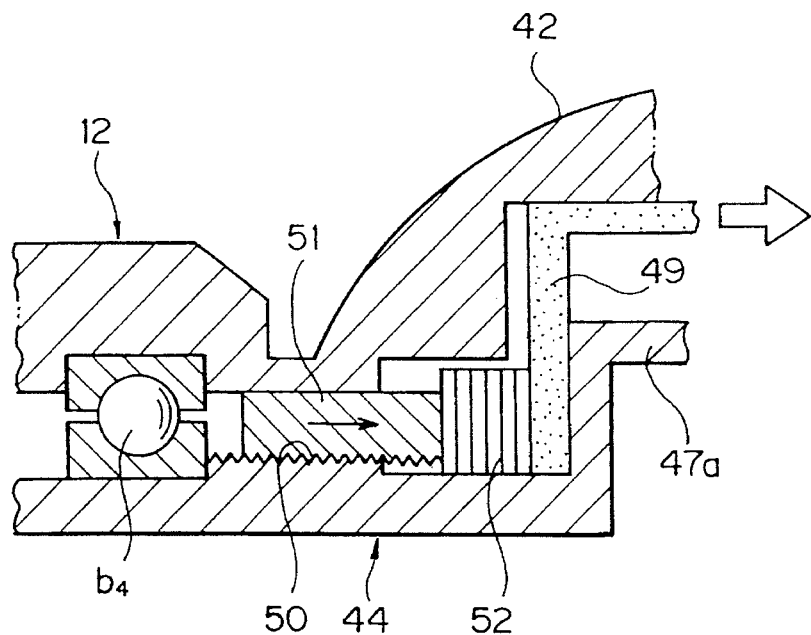
FIG. 5 is an enlarged cross-sectional view showing a movable barrel and a pressure spring assuming a locked state.
Figure 6:
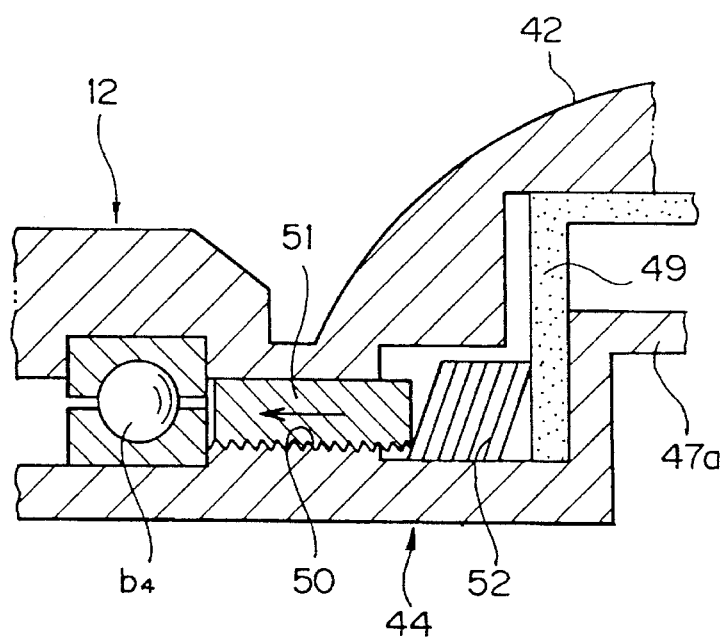
FIG. 6 is an enlarged cross-sectional view showing the movable barrel and the pressure spring shown in FIG. 5 assuming an unlocked state.

Vertical Part 8 (see mainly FIG. 4)

An inner barrel 20 formed integrally with the horizontal part 9 is rotatably connected via bearings $b_1$ on the top of the vertical part 8 to allow the horizontal part 9 (as well as, the arm supporting section 11 and the holding arm 15, entirely) to be rotatable horizontally on the axis α. The vertical part 8 is integrated with a bevel gear 21.

Figure 2:
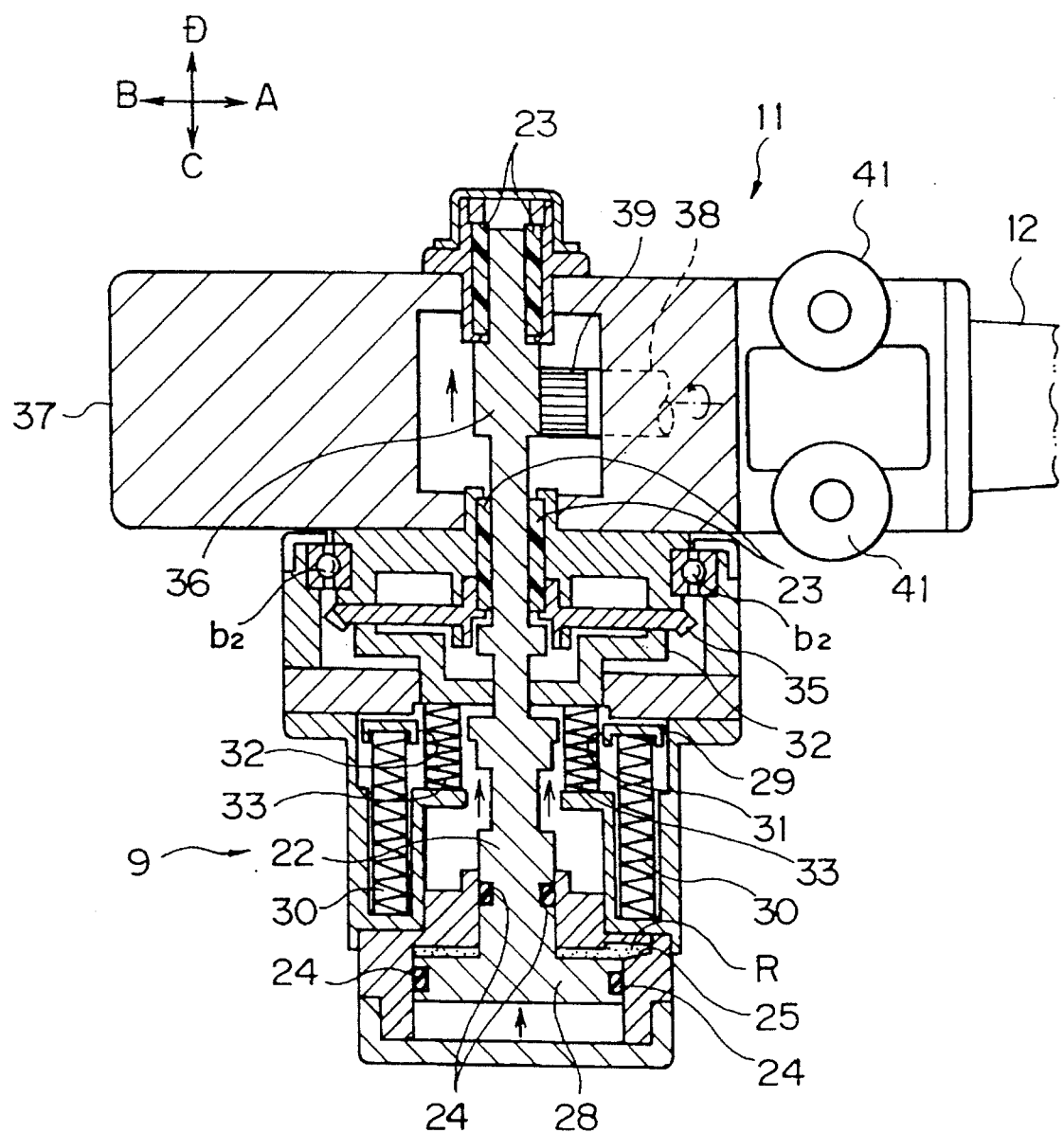
FIG. 2 is a cross-sectional view of a horizontal part assuming .a locked state, taken along the line SA—SA of FIG. 1.
Figure 3:
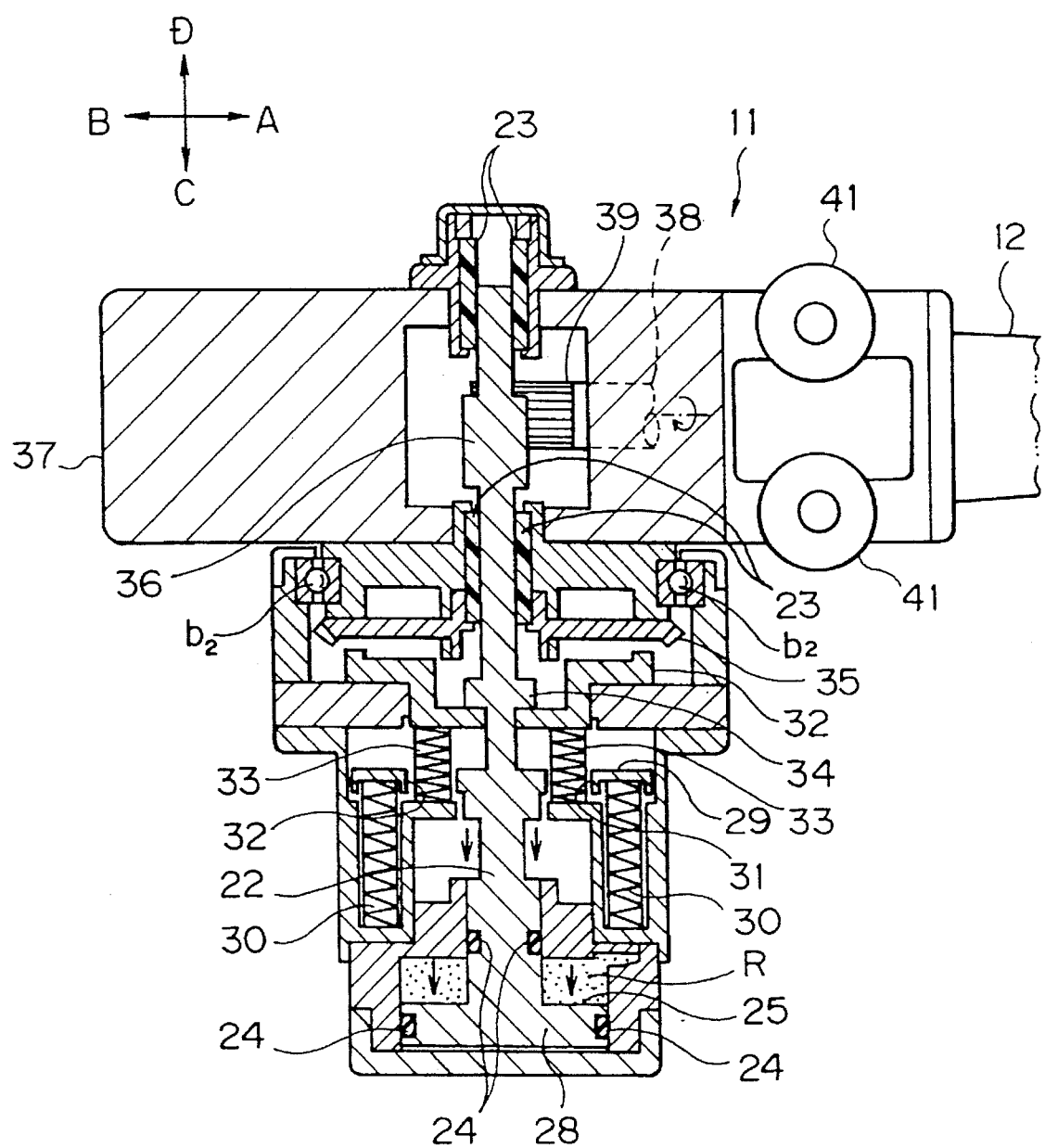
FIG. 3 is a cross-sectional view of the horizontal part shown in FIG. 2 assuming an unlocked state.

Horizontal Part 9 (see mainly FIGS. 2 and 3)

The arm supporting section 11 is rotatably connected to the side D of the horizontal part 9 via a bearing $b_2$ to allow the arm supporting section 11 (as well as, the entire holding arm 15) to be rotatable vertically on the axis β. A piston 22 is disposed in the horizontal part 9 to penetrate it and extend into the arm supporting section 11. The piston 22 is supported by bushings 23 and oil seals 24 to be reciprocatable between the directions C and D. FIG. 2 shows a state where the piston 22 is moved in the direction D, i.e. rightward; while FIG. 3 shows a state where the piston 22 is moved in the direction C, i.e. leftward.

The horizontal part 9 has on the side C a cylinder section 25 to which a hydraulic hose 27 (see FIG. 1) extending from a power supply and hydraulic control unit 26 is connected such that an oil R can be pumped through the hydraulic hose 27 into the cylinder section 25. Meanwhile, the distal end portion 28 of the piston 22 is located in this cylinder section 25 such that the portion 28 can be pushed in the direction C by the pressure of the oil R pumped into the cylinder section 25. The piston 22 has a disc-like flange 29 formed at the intermediate thereof, and a plurality of coil springs 30 (urging means) are interposed between the flange 29 and the cylinder section 25 to be arranged horizontally in the circumferential direction of the horizontal part 9. These coil springs 30 urge the piston 22 entirely in the direction D.

The flange 29 contains a plurality of circular holes 31 arranged in the circumferential direction, in which coil springs 33 are disposed respectively. These springs 33 urges a ring 32 fitted with play on the piston 22 in the direction D. The ring 32 engages with an annular ridge 34 of the piston 22 to be moved together with the piston 22 when the piston moves in the direction C.

Further, a bevel gear 35 is fitted with play on the piston 22 at a position between the ring 32 and the arm supporting section 11. The bevel gear 35 meshes with the bevel gear 21 of the vertical part 8. A rack 36 is formed at the proximal end portion of the piston 22. The rack 36 includes a plurality of grooves formed circumferentially.

Arm Supporting Section 11 (see mainly FIG. 4)

A counter weight 37 balancing the weight of the holding arm 15 is fixed to the rear end side of the arm supporting section 11. The arm supporting section 11 contains a pivotal shaft 38 supported pivotally via bearings $b_3$. A pinion gear 39, which is meshed with the rack 36 of the piston 22, is attached to the rear end of the pivotal shaft 38. The front end portion of the pivotal shaft 38 is also provided with another pinion gear 40. The rear end portion of the first arm 12 is removably attached to the arm supporting section 11 by a couple of screws 41.

First Arm 12 and Second Arm 13 (see mainly FIG. 4)

The first arm 12 and the second arm 13 generally have tubular forms. The first arm 12 has an inner ball 42 formed at the front end, whereas an outer ball 43 is formed at the rear end of the second arm 13. The inner ball 42 is slidably fitted in the outer ball 43 to constitute the first joint 16. A first pivotal axis 44 and a second pivotal axis 45 which have thin tubular forms are disposed pivotally in the first arm 12 and the second arm 13 via bearings $b_4$, respectively. A pinion gear 46 is formed at the rear end portion of the first pivotal axis 45, so that the pinion gear 46 may be meshed with the pinion gear 40 formed at the front end portion of the pivotal shaft 38 when the first arm 12 is attached to the arm supporting section 11 with screws 41.

Figure 8:
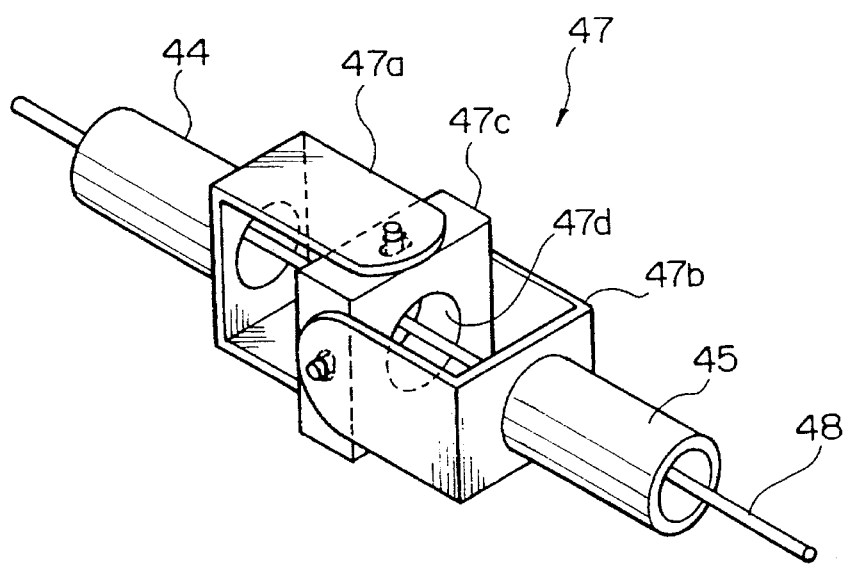
FIG. 8 is an enlarged perspective view of a universal coupling section.

The first pivotal axis 44 and the second pivotal axis 45 are connected to a universal coupling section 47 (see FIG. 8) in the first joint 16 such that the turning force of the first pivotal axis 44 will be transmitted directly to the second pivotal axis 45. More specifically, the first pivotal axis 44 and second pivotal axis 45 have at the ends respectively rectangular U-shaped brackets 47a,47b which are opposed perpendicular to each other and pivotally mounted to an intermediate member 47c. Accordingly, the turning force of the first pivotal axis 44 can securely be transmitted to the second pivotal axis 45 no matter how the angle formed between the first arm 12 and the second arm 13 may be changed. The intermediate member 47c contains an opening 47d which allows passage of a wire 48 extended through the first pivotal axis 45 and the second pivotal axis Further, a clutch 49, which is engaged with the rectangular U-shaped bracket 47a, is attached to the end portion of the first pivotal axis 44 located in the first joint 16. The clutch 49, when pushed forward, is brought into press contact with the inner surface of the outer ball 43 to lock the first joint 16.

The first pivotal axis 44 has an external thread 50 formed behind the clutch 49, and a movable barrel 51 is fitted to engage with the external thread 50. A pressure spring 52 formed by laminating six belleville springs is interposed between the movable barrel 51 and the clutch 49. Handle 14 and switch mechanism (see mainly FIG. 4):

The second arm 13 and the handle 14 are connected to each other at the second joint 17. The second joint 17 is of the same structure as the first joint 16 and contains a clutch 53, a movable barrel 54, an external thread 55 and a pressure spring 56 (provided that the pressure spring 56 consists of three belleville springs). The brain spatula 18 is attached to the free end portion of the handle 14. The position of the brain spatula 18 can be adjusted finely in the vertical direction by turning an adjust screw 57 (see FIG. 1) locating at the free end portion of the handle 14 and in the horizontal direction by turning another adjust screw 58, and thus the brain spatula 18 can be turned and immobilized at a desired position.

The pair of levers 19 disposed on the handle 14 are incorporated with a pair of links 59 which are connected to each other at the middle of the levers 19, respectively. The connecting point 59a of the links 59 is designed to be shifted forward by a predetermined stroke by holding the levers 19 closer to each other. A spring 60 is extended across the levers 19. The spring 60 normally urges the levers 19 to open at the free end portions by a predetermined degree.

The terminal of the wire 48 is connected to the connecting point 59a of the links 59. The wire 48 extends from the handle 14 passing through the second pivotal axis 45 and first pivotal axis 44 and is connected to one end of a sensor 61 locating on the rear end portion of the first pivotal axis 45. The other end of the sensor 61 is pulled by a spring 62 retained on the arm supporting section. The tensile force of the spring 62 is designed to be smaller than that of the spring 60 to open the free end portions of the levers 19 by a predetermined angle.

Figure 7:
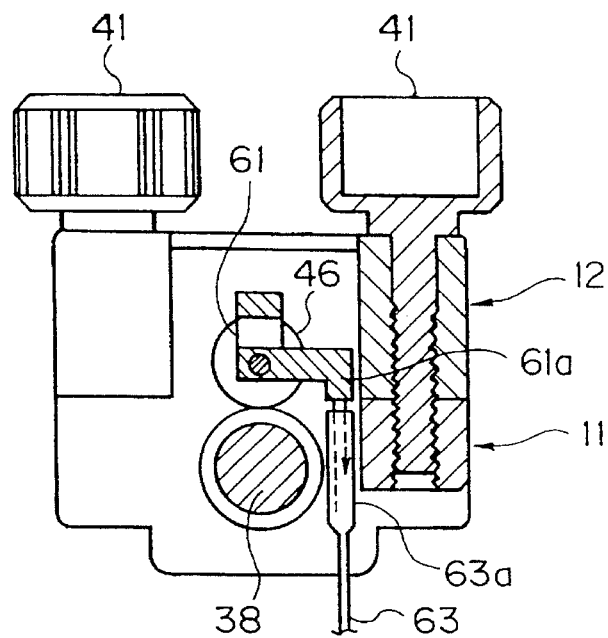
FIG. 7 is a cross-sectional view taken along the line SB—SB of FIG. 4.

The sensor 61 has a protrusion 61a bending downward (see FIG. 7) from one side, and the terminal 63a of a fiber photoelectric cable 63 is positioned below the lower end of the protrusion 61a. The fiber photoelectric cable 63, as well as the hydraulic hose 27, is connected to the power supply and hydraulic control unit 26 (driving means) (see FIG. 1). When the protrusion 61a of the sensor 61 is located immediately above the terminal 63a of the fiber photoelectric cable 63, i.e. when the protrusion 61a is blocking the terminal 63a of the cable 63, the light coming from the terminal 63a is reflected back to the terminal 63a and runs directly through the fiber photoelectric cable 63 to be detected by the power supply and hydraulic control unit 26. Thus, it can be found out that the protrusion 61a is located immediately above the terminal 63a. If the protrusion 61a is not located immediately above the terminal 63a, the light coming from the terminal 63a is not reflected back to the terminal 63a. Thus, it can be found out that the protrusion 61a is not located immediately above the terminal 63a. The protrusion 61a is designed to move forward, when the levers 19 of the handle 14 are pressed, to locate immediately above the terminal 63a and to deviate from that location when the levers 19 are not pressed. Further, the oil R is adapted to be pumped into the cylinder section 25 of the horizontal part 9 from the power supply and hydraulic control unit 26 only when it is detected by the unit 26 that the protrusion 61a is located immediately above the terminal 63a.

Next, operation of the internal structure of the holding arm 15 will be described with respect to the locked and unlocked states, respectively.

Locked State

In the normal state where the holding arm 15 is not touched, the axis α of the vertical part 8, the axis β of the horizontal part 9, the first joint 16 and the second joint 17 assume locked states, respectively, to maintain a state where the brain spatula 18 is securely held. More specifically, when the switch levers 19 of the handle 14 are not touched, the protrusion 61a of the sensor 61 is deviated from the terminal 63a of the fiber photoelectric cable 63. Accordingly, no oil R is fed from the power supply and hydraulic control unit 26 into the cylinder section 25 of the horizontal part 9, and the holding arm 15 is subject only to the forces of the coil springs 30,33 disposed in the horizontal part 9. That is, as shown in FIG. 2, since the inner coil springs 33 push the ring 32 in the direction D, the bevel gear 35 of the horizontal part 9 is held tightly between the ring 32 and the associated portion of the arm supporting section 11 to be unrotatable. The bevel gear 21 of the vertical part 8, which also engages with the bevel gear 35 of the horizontal part 9, becomes unrotatable likewise, thus locking rotation of the vertical part 8 and horizontal part 9 on the axes α and β, respectively.

Further, since the flange 29 of the piston 22 is pushed by the outer coil springs 30 in the direction D, the pinion gear 39 of the pivotal shaft 38 is turned counterclockwise in a forward view by the rack 36 of the piston 22. Since the pinion gear 40 at the front end portion of the pivotal shaft 38 and the pinion gear 46 of the first pivotal axis 45 are meshed with each other, the turning of the pivotal shaft 38 is transmitted to the first pivotal shaft 44 to turn the first pivotal shaft 44 clockwise in a forward view. When the first pivotal shaft 44 is turned clockwise, the movable barrel 51 engaged with the external thread 55 formed at the front end portion of the first pivotal shaft 44 is moved forward to push the pressure spring 52. Accordingly, the clutch 49 is pushed forward by the pressure spring 52 to be brought into strong press contact with the inner surface of the outer ball 43, and thus the first joint 16 is locked. Since such turning force of the first pivotal shaft 44 is also transmitted via the universal coupling section 47 to the second pivotal axis 45, the second joint is locked as well as the first joint 16. Thus, the holding arm 15 assumes a completely locked state to hold the brain spatula 18 securely. Since the first pivotal shaft 44 and second pivotal axis 45 are normally urged by the strong coil springs 30, the position and angle of the brain spatula 18 do not change with time. In addition, both the coil springs 33 pressing the bevel gear 35 and the coil springs 30 urging the piston 22 in the direction D are arranged in the circumferential direction of the horizontal part 9. Accordingly,. if there occurs any trouble in some of these springs, some degrees of locking function can be secured by the rest of the coil springs 30,33 in this embodiment. Such constitution is advantageous in the aspect of safety.

Unlocked State

When the levers 19 of the handle 14 are gripped so as to change the position or angle of the brain spatula 18, the levers 19 are pulled closer to each other to shift the connecting point 59a of the links 59 forward and pull the wire 48 forward. When the wire 48 is pulled forward, the sensor 61 connected to the rear end of the wire 48 moves forward to allow the protrusion 61a to locate immediately above the terminal 63a of the fiber photoelectric cable 63. Since the light coming out of the terminal 63a impinges upon the protrusion 61a and travels back along the fiber photoelectric cable 63, the light is detected by the power supply and hydraulic control unit 26, and the oil R is pumped through the hydraulic hose 27 into the cylinder section 25. When the oil R is pumped into the cylinder section 25, the distal end portion 28 of the piston 22 is pushed in the direction C to move the piston 22 in the direction C against the urging force of the coil springs 30.

When the piston 22 is moved in the direction C, the ring 32 engaging with the annular ridge 34 is pushed in the direction C to release holding of the bevel gear 35 to allow the bevel gear 35 and the bevel gear 21 of the vertical part 8 engaged therewith to assume unlocked states. Accordingly, the vertical part 8 and the horizontal part 9 can be moved freely on the axes α, β, respectively.

When the piston 22 is moved in the direction C, the pivotal shaft 38 engaged with the rack 36 of the piston 22 rotates clockwise to turn counterclockwise the first pivotal axis 44 engaged with the pivotal shaft 38. The counterclockwise rotation of the first pivotal axis 44 moves the movable barrel 51 engaged with the external thread 50 formed on the first pivotal axis 44 backward (in the direction B) to release pressing of the pressure spring 52. Since the press contact of the clutch 49 against the outer ball 43 is thus released, the first joint 16 assumes a free state, i.e. unlocked state. Incidentally, since there is a certain degree of sliding resistance between the inner ball 42 and the outer ball 43 even after the press contact by the clutch 49 is released, the holding arm 15 does not assume an excessively unlocked state, and an appropriate sliding resistance for operating the holding arm 15 can be reserved. Further, since the second pivotal axis 45 rotates like the first pivotal axis 44, the second joint 17 also assumes an unlocked state. As described above, since the rotary section 10 and the holding arm 15 spontaneously assume unlocked states merely by holding the handle 14 with one hand and pressing the levers 19, the position and angle of the brain spatula 18 can freely be changed. The rotary section 10 and the holding arm 15 momentarily resume the locked states by releasing holding of the levers 19 after the position or angle of the brain spatula 18 is changed, thus allowing very easy operation. Besides, by virtue of the counter weight 37 balancing the weight of the holding arm 15, provided on the arm supporting section 11, it does not require much force to move the holding arm 15 assuming the unlocked state.

The holding arm 15 according to this embodiment enjoys another characteristic, in addition to the good operability as described above, that it is electrically insulated. More specifically, while the levers 19 of the handle 14 are serving as a switch for the driving means (power supply and hydraulic control unit 26) which feeds an oil R, the rotary section 10, the arm supporting section 11, and the holding arm 15 are free from electric system. Accordingly, even if the holding arm 15 etc. should touch the body of the patient 2 during surgery, there is no possibility that the patient 2 is affected by electricity. In short, the possibility that electric current flows across the holding arm 15 or brain spatula 18 is absolutely obviated by employing a nonelectric signal transmission routes, i.e. the wire 48 and fiber photoelectric cable 63. Further, since the holding arm 15 is adapted to be detachable from the arm supporting section 11 by loosening the screws 41 and also assumes a nonelectric structure as described above, the holding arm 15 thus detached can as such be subjected to sterilization.

As described above, according to the holding arm 15 in this embodiment, the brain spatula 18 can be held securely at a desired position with no reduction in the holding force with time, and also the holding position can easily be changed. Further, since no electric system is employed, there is no fear of electrical accident, and the holding arm 15 can be sterilized.

It should be noted here while hydraulic pressure is employed as the driving means for moving the piston 22 against the resilience of the coil springs 30 in the above embodiment, the present invention is not limited to this, and a general air motor etc. may be employed. While it is possible to use an ordinary electric motor, the nonelectrical characteristics described above cannot be obtained.

While two arms, i.e. the first arm 12 and the second arm 13, are employed in the above embodiment, the holding arm 15 may consist of three or more arms which are connected by joints. Further, while a pair of levers 19 are disposed in the above embodiment, the number of levers 19 may be only one.

As has been described heretofore, according to the present invention, a tool or device can be held securely at a desired position with no reduction in the holding force, and also the holding position can be changed easily. Further, the holding arm can be operated with one hand, and after the holding arm is set in position, the surgeon can concentrate on his operation using tools with both his hands. Thus, the holding arm holds the tool or device securely as if an assistant does, and the position and the angle of the tool or device can easily be changed.

Meanwhile, if the holding arm is designed to use no electric system, there is no fear of electrical troubles, and also the holding arm can be sterilized. Since the holding arm has a structure such that it normally assumes a locked state, and an unlocked state only when necessitated, the locked state of the arm can be maintained even if any trouble occurs in the driving means, causing no falling of the holding arm.

What is claimed is:

1. An articulated-tool holding arm comprising:

a plurality of tubular arms connected to one another at joints each consisting of an outer ball and an inner ball slidably fitted therein;

a handle for holding a tool, attached to the foremost end of the thus connected tubular arms;

pivotal axes penetrating said arms such that said axes may be connected to one another at the end portions in said joints, respectively, to be able to transmit turning motions to one another;

a clutch disposed to either said inner ball or said outer ball in each joint, said clutch being pressed by a pressure spring to be brought into contact with the other ball; and a movable barrel engaged with an external thread formed near the end portion of each pivotal axis;

wherein each of said pivotal axes is designed to be normally urged to turn in one direction by an urging means to allow said movable barrel to press said pressure spring; whereas the pressure applied to said pressure spring by said movable barrel is adapted to be releasable by turning said pivotal axis by a driving means in the opposite direction against the urging force of said urging means.

2. The articulated tool-holding arm according to claim 1, wherein said urging means for turning each pivotal axis in one direction is a plurality of coil springs, and said driving means for turning said pivotal axis in the opposite direction is hydraulic pressure.

3. The articulated tool-holding arm according to claim 1, wherein said handle is provided with a couple of levers which form a predetermined angle and also a pair of links having a connecting point which shifts when said levers are held closer to each other, with a wire being connected at one end to said connecting point and inserted through said pivotal axes; and said driving means for turning said pivotal axes in the opposite directions is controlled at the other end of said wire.

4. The articulated tool-holding arm according to claim 2, wherein said handle is provided with a couple of levers which form a predetermined angle and also a pair of links having a connecting point which shifts when said levers are held closer to each other, with a wire being connected at one end to said connecting point and inserted through said pivotal axes; and said driving means for turning said pivotal axes in the opposite directions is controlled at the other end of said wire.

* * * * *

UNITED STATES PATENT AND TRADEMARK OFFICE
CERTIFICATE OF CORRECTION

PATENT NO.    : 5,609,565
DATED         : March 11, 1997
INVENTOR(S)   : Katsushige NAKAMURA It is certified that error appears in the above-identified patent and that said Letters Patent is hereby corrected as shown below:

On the cover page, Item [30], under Foreign Application Priority Data, "Sept. 8, 1994" should read --August 9, 1994--.

Signed and Sealed this

Twenty-ninth Day of July, 1997

*Attest:*

BRUCE LEHMAN

*Attesting Officer*      *Commissioner of Patents and Trademarks*